(12) United States Patent
MacInnis et al.

(10) Patent No.: US 6,481,290 B1
(45) Date of Patent: Nov. 19, 2002

(54) METHOD AND APPARATUS FOR ULTRASONIC NON-DESTRUCTIVE INSPECTION

(75) Inventors: Timothy John MacInnis, Quaker Hill, CT (US); Willard Clark Nichols, Niantic, CT (US); Dean Emerson Christie, Groton, CT (US)

(73) Assignee: Science Applications International Corporation, San Diego, CA (US)

( * ) Notice: Subject to any disclaimer, the term of this patent is extended or adjusted under 35 U.S.C. 154(b) by 0 days.

(21) Appl. No.: 09/871,707

(22) Filed: Jun. 4, 2001

(51) Int. Cl.$^7$ ............................................... G01N 29/00
(52) U.S. Cl. ....................................................... 73/644
(58) Field of Search .......................... 73/632, 633, 634, 73/644

(56) References Cited

U.S. PATENT DOCUMENTS 4,796,632 A    1/1989  Boyd et al.
4,813,402 A    3/1989  Reichenberger et al.
5,469,744 A    11/1995 Patton et al.
6,298,727 B1 * 10/2001 Fleming et al. ............... 73/644

\* cited by examiner

Primary Examiner—Richard A. Moller
(74) Attorney, Agent, or Firm—Banner & Witcoff, Ltd.

(57) ABSTRACT

A method and apparatus for non-destructive inspection is provided. An automatic couplant delivery system that delivers and maintains a constant water supply to a single path chamber located at a transducer head. Any couplant run-off is removed and reclaimed by vacuum recovery. A transducer holder block that supports two transducers is used, and mounts to a manifold and brush subassembly. A manifold and brush subassembly includes a manifold block, a couplant containment/removal block, and gimbal. The manifold and brush subassembly has three sets of brushes that define three chambers for water or vacuum. An innermost chamber sets the water path, the middle chamber may provide water or regulated vacuum, and the outer chamber provides full vacuum for water removal. Couplant flow rate and vacuum are selectable and can be adjusted by an operator during initial set up.

54 Claims, 7 Drawing Sheets

METHOD AND APPARATUS FOR ULTRASONIC NON-DESTRUCTIVE INSPECTION

BACKGROUND OF THE INVENTION

1. Field of the Invention

The present invention relates to a method and apparatus for ultrasonic non-destructive inspection. More particularly, the present invention is directed to a method and apparatus for ultrasonic inspection having improved electronic coupling between a transducer and the surface of the object under inspection.

2. Description of the Prior Art

Many machines and vehicles experience wear and part degradation during their useful lives, which gets worse as they age. Ultimately such wear can result in complete failure. Depending upon the machine or vehicle, such failure can be catastrophic. For example, for aircraft, a failure in mid-flight may be deadly.

In order to counter the effects of aging and prolong the effective lives of such machines and vehicles, regimens of regular inspection and maintenance have been put in to practice. While some machines and parts of some vehicles can be inspected and maintained easily, wear and fatigue to some parts and vehicles is difficult to discover, as it may not be visible to the naked eye, and/or be located in an easily accessible location.

Consequently, inspection of such parts and vehicles may be very laborious, expensive and time-consuming. Significant disassembly and reassembly may be required, and the inspection may require considerable test equipment. Previously, regular inspection has often been destructive in the sense that portions of the device or vehicle had to be expended in order to perform a complete inspection. Such destructive examination is extremely expensive and can often be very time consuming.

In an attempt to overcome the drawbacks of such destructive inspection, non-destructive inspection (NDI) has been developed. NDI is typically performed by subjecting the device to be inspected with acoustic waves and then analyzing the reflected waves to determine the state of the device without causing damage to the device. Acoustic NDI is particularly suited for determining the integrity of airplane components. Conventional acoustic NDI equipment emits acoustic waves through a transducer. The reflected acoustic waves are received by the transducer, which produces an electrical signal that is subsequently analyzed to rate the status of the workpiece.

Over time aircraft experience fatigue as a result of normal use of the aircraft. Such fatigue often manifests itself as cracking. In order to prevent failure of the aircraft, which may result in the loss of life, the aircraft are regularly inspected to determine the integrity of the aircraft and to assess the extent of any fatigue experienced by any parts of the aircraft.

An apparatus for acoustically inspecting a workpiece is taught in U.S. Pat. No. 5,469,744 (Patton et al.). The apparatus disclosed in the Patton et al. patent is known as a contact adaptive bubbler. As noted in the Patton et al. patent, ultrasonic NDI can improve the inspection spatial resolution and signal to noise ratio by using a focused acoustic beam. However, to be reasonably effective an ultrasonic transducer needs a good acoustic coupling between the transducer and the workpiece. Water is typically used as a coupling fluid between the workpiece and the transducer, and is sent through a perforated membrane to come in contact with the workpiece.

In order to better control the flow of coupling fluid, the Patton et al. apparatus uses a non-perforated membrane, and two fluid chambers. The non-perforated membrane separates the two chambers. The lower chamber is formed when the apparatus is placed adjacent the workpiece, and can conform somewhat to the shape of the workpiece. The lower chamber is smaller than the upper chamber to provide control of the water flow as compared to an apparatus having a perorated membrane, since apparatus with perforated membranes cannot control the amount of fluid leaking through the membrane.

Conventional bubbler systems including the Patton et al. apparatus utilize a membrane between the transducer and the workpiece to contain the water and reduce air bubble activity. The use of a membrane in such systems creates a drawback, namely the introduction of additional attenuation to the ultrasonic signal.

Furthermore, conventional bubbler systems require a relatively high water flow rate to maintain the water path requirements of automated canning. Such high flow rates are not conducive to efficient couplant removal.

Another drawback, in particular for the inspection of the upper surfaces of aircraft, is that conventional bubblers do not have sufficient couplant recovery and leave significant water residue, which can be a safety hazard.

SUMMARY OF THE INVENTION

The deficiencies of the conventional methods are addressed by the present invention that is directed to a method and apparatus for non-destructive inspection. In particular, the method and apparatus of the present invention use an automatic couplant delivery system that delivers and maintains a constant water supply to a single path chamber located at the transducer head. Any couplant run-off is removed and reclaimed by vacuum recovery. A transducer holder block that supports two transducers is used, and mounts to a manifold and brush subassembly.

The manifold and brush subassembly includes a manifold block, a couplant containment/removal block, and gimbal. The manifold and brush subassembly has three sets of brushes that in turn provide three chambers for water or vacuum. An innermost chamber sets the water path, the middle chamber may provide water or regulated vacuum, and the outer chamber provides full vacuum for water removal. The bottoms of the transducers are positioned below the upper surface of the water chamber to allow air bubbles to naturally migrate to the highest point and then evacuate through a vacuum port. Such a configuration eliminates the need for a membrane containment area and then an additional containment chamber. Couplant flow rate and vacuum are selectable and can be adjusted by an operator during initial set up.

An advantage of the method and apparatus of the present invention is that no membrane is needed to contain the couplant in the acoustic transducer apparatus.

Another advantage of the method and apparatus according to the present invention is that additional attenuation is reduced.

Yet another advantage of the method and apparatus according to the present invention is that a majority of any excess couplant is removed.

Still another advantage of the method and apparatus according to the present invention is that the apparatus can be configured for operation above and below a workpiece.

Another advantage of the method and apparatus according to the present invention is that interference from upwardly migrating bubbles is reduced.

BRIEF DESCRIPTION OF THE DRAWINGS

These and other attributes of the present invention will be described with respect to the following drawings in which.

DETAILED DESCRIPTION OF THE INVENTION

Figure 11:
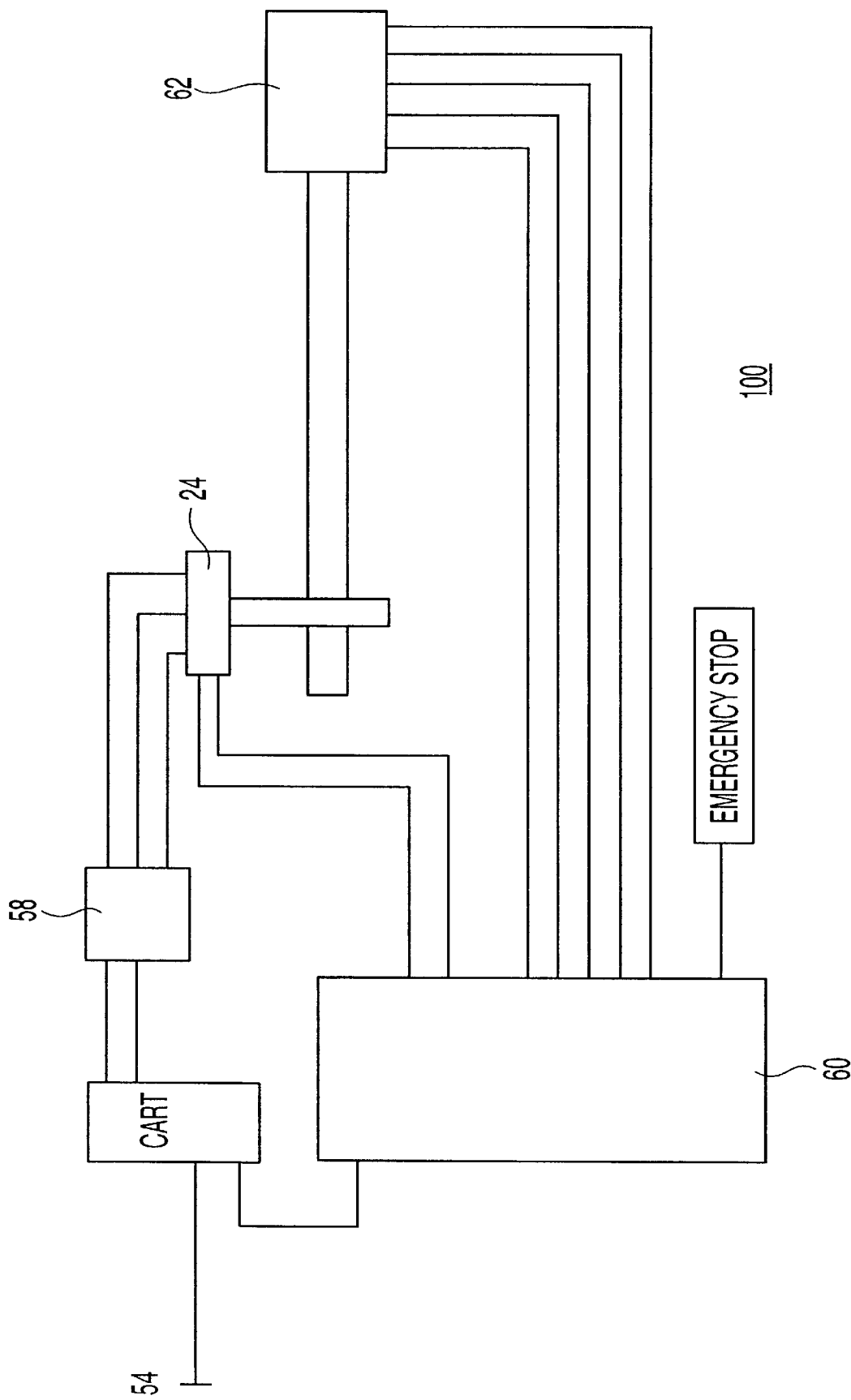
FIG. 11 is a block diagram illustrating the various components of the ultrasonic inspection apparatus according to the present invention.

The ultrasonic inspection apparatus 100 of the present invention, shown in FIG. 11, is designed to inspect machines such as airplanes. One area of an airplane that can be inspected using the ultrasonic inspection apparatus 100, for example, is the wingspan fasteners (i.e. splice joints) used to connect various section of the wing assembly of an airplane. The ultrasonic inspection apparatus 100 of the present invention can inspect and detect fatigue cracks at or near the fastener sites. In addition, the ultrasonic inspection apparatus of the present invention can be used for corrosion inspection.

The ultrasonic inspection apparatus 100 is designed to operate in conjunction with an automated scanner 62, such as one manufactured by TIEDM. Such automatic scanners can move the ultrasonic inspection apparatus through a prescribed path over the surface of the workpiece. Typically the path is linear and the automatic scanner includes guide rails that are held to the surface of the workpiece with suction cups. If the ultrasonic inspection apparatus 100 is being used to inspect the wingspan fasteners of an aircraft, the automatic track is deployed so that the ultrasonic inspection apparatus 100 moves over the length of the splice joint.

Figure 1:
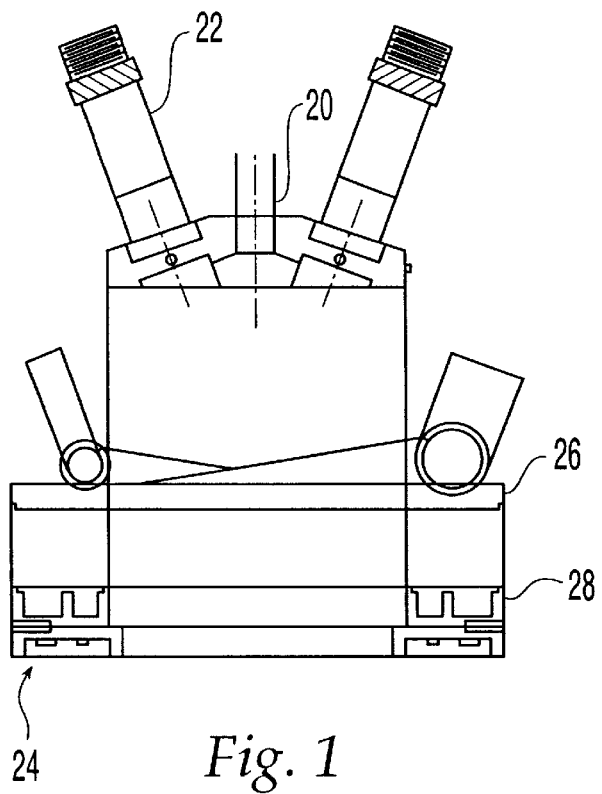
FIG. 1 is a partially exploded side cross-sectional view of a couplant/vacuum head of the ultrasonic inspection apparatus of the present invention.

Referring to the side cross-sectional view shown in FIG. 1, the ultrasonic inspection apparatus of the present invention includes a transducer holder block 20, one or two acoustic transducers 22, and a couplant/vacuum head 24 that includes a manifold 26 and brush subassembly 28. The transducer holder block 20, shown in phantom, fits into the manifold 26, as shown in the side view of FIG. 2.

Figure 2:
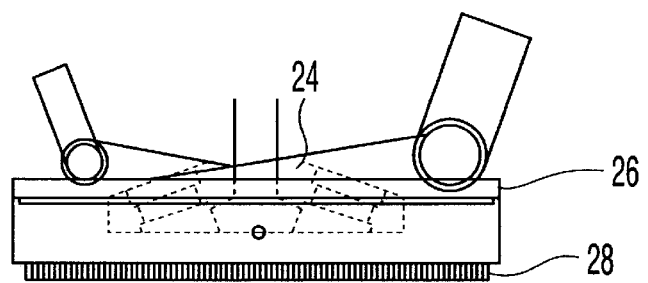
FIG. 2 is a side view of a couplant/vacuum head of the ultrasonic inspection apparatus of the present invention.

While only one transducer 22 is shown in FIGS. 1 and 2, the transducer holder block 20 is configured to support two transducers 22. In the embodiment shown in FIGS. 1 and 2, the transducers 22 are supported at an angle by the transducer holder block 20. A preferred angle for the transducers 22 is 20°. In this manner the two transducers 22 have converging focal points so that the two transducers 22 simultaneously inspect the same point. In a preferred embodiment, the angled configuration is used for fastener inspection, and the transducers 22 are immersion transducers.

Figure 3:
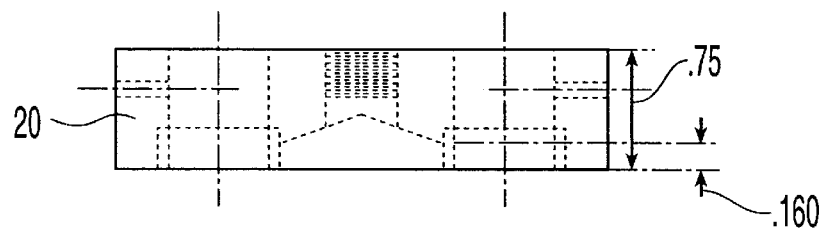
FIG. 3 is a side view of an alternative configuration for the transducer holder block, according to the present invention.

FIG. 3 shows an alternative configuration for the transducer holder block 20. Instead of being supported at an angle like the embodiment shown in FIGS. 1 and 2, the transducer holder block 20 shown in FIG. 3 supports the two transducers perpendicular to the surface being scanned. The transducers are preferably ultrasonic transducers. The configuration shown in FIG. 3 is designed to inspect for corrosion.

Figure 4:
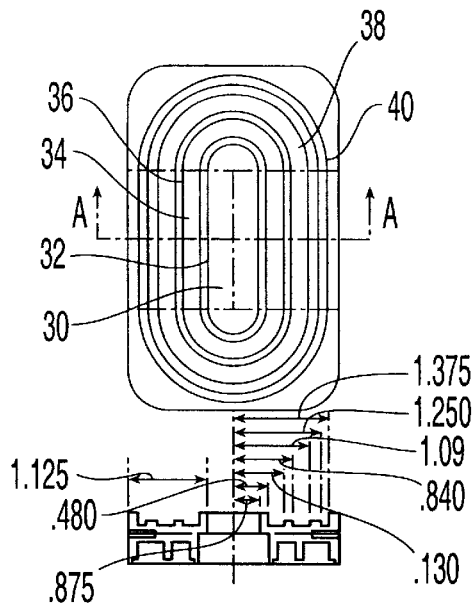
FIG. 4 is a bottom view of the couplant/vacuum head of the ultrasonic inspection apparatus of the present invention.

The couplant/vacuum head 24 is designed to provide a three-region system for automatic couplant delivery and removal. FIG. 4 is a bottom view of the ultrasonic inspection apparatus 100 shown in FIGS. 1 and 2. The couplant (e.g. water) is provided as the transmission medium between the test surface and the transducer(s) 22. Referring to FIGS. 2 and 4, an innermost transducer region 30 is created by an elongated annular inner brush seal 32; An intermediate region 34 is created by a larger, elongated annular, middle brush seal 36 spaced outwardly from the inner brush seal 32; and an outermost recovery region 38 is created by a still larger, elongated annular, outer brush seal 40 spaced outwardly from the middle brush seal 36.

The brush seals 32, 36, and 40 have a thickness and length, and are made from a material that provides sufficient sealing with a test surface to minimize couplant leakage while accommodating surface variations.

The innermost transducer region 30 determines the couplant flow path. The intermediate region 34 may provide water or regulated vacuum, and the outermost recovery region 38 provides full vacuum for couplant removal.

Figure 5:
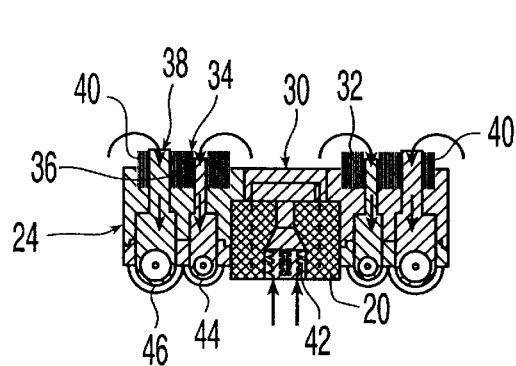
FIG. 5 is a cross-sectional side view of the ultrasonic inspection apparatus of the present invention configured for lower surface scanning.
Figure 6:
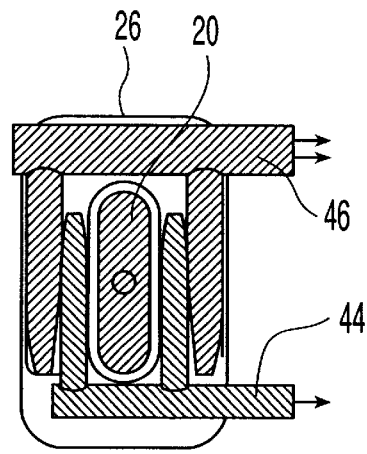
FIG. 6 is a top view of the ultrasonic inspection apparatus of the present invention configured for lower surface scanning.

The flow path is selected based upon whether the surface being inspected is an upper or lower surface. Referring to FIGS. 5 and 6, a cross-sectional side view and a top view of the couplant/vacuum head 24, respectively, are shown and illustrate the couplant flow path for lower surface inspection. Couplant flows into the port 42 at the bottom of the transducer holder block 20, from a pump 56, shown in FIGS. 9 and 10.

The couplant rises to fill the cavity of the innermost transducer region 30 and then flows outwards over the elongated annular inner brush seal 32 into the intermediate region 34. The intermediate region 34 is connected to a vacuum 54 so that the overflowing couplant from the innermost transducer region 30 is drawn from the surface and is returned. The tubes 44 through which the couplant is drawn have a relatively small diameter compared to the diameter of the tubes 46 connected to the outermost recovery region 38, discussed below.

Any couplant that flows over the intermediate brush seal 36, spaced outwardly from the inner brush seal 32, enters the outermost recovery region 38 formed by the outer brush seal 40 spaced outwardly from the intermediate brush seal 36. Like the intermediate region 34, the outermost recovery region 38 is connected to a vacuum source 54. The tubes 46 leading from the outermost recovery region 38 have a larger diameter than the diameter of the tubes 44 leading form the intermediate region 34 in order to provide high airflow. The airflow carries the excess couplant back to the supply tank 58 and dries the surface of the workpiece being inspected.

As a result of the foregoing configuration, any couplant that overflows the inner elongated annular inner brush seal 32 or the intermediate brush seal 36 due to surface irregularities or raised fastener heads is recovered in both the intermediate and outermost regions that are connected to the vacuum 54.

Figure 7:
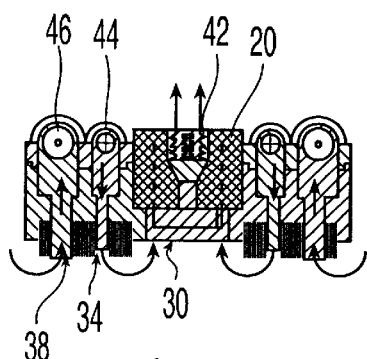
FIG. 7 is a cross-sectional side view of the ultrasonic inspection apparatus of the present invention configured for upper surface scanning.
Figure 8:
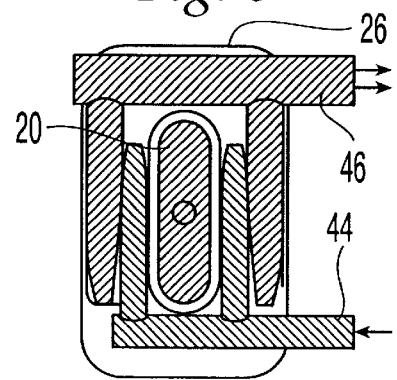
FIG. 8 is a top view of the ultrasonic inspection apparatus of the present invention configured for upper surface scanning.

Referring to FIGS. 7 and 8, a cross-sectional side view and a top view of the couplant/vacuum head 24, respectively, are shown and illustrate the couplant flow path for upper surface inspection. Couplant is supplied through the tubes 44 to the intermediate region 34. Both the innermost transducer region 30 and the outermost recovery region 38 are connected to a vacuum 54. Excess couplant flowing into the outermost recovery region 38 is drawn back through the tubes 46 to the couplant supply source 58 by the high airflow created by the vacuum 54. Similarly, couplant that flows inwards under the inner brush seal 32 is drawn through the port 42 in the transducer holding block 20 by the vacuum 54.

For upper surface scanning the transducers 22 are set below the upper surface of the couplant so that bubbles will migrate naturally to the upper surface where they are evacuated through the vacuum port 42.

Figure 9:
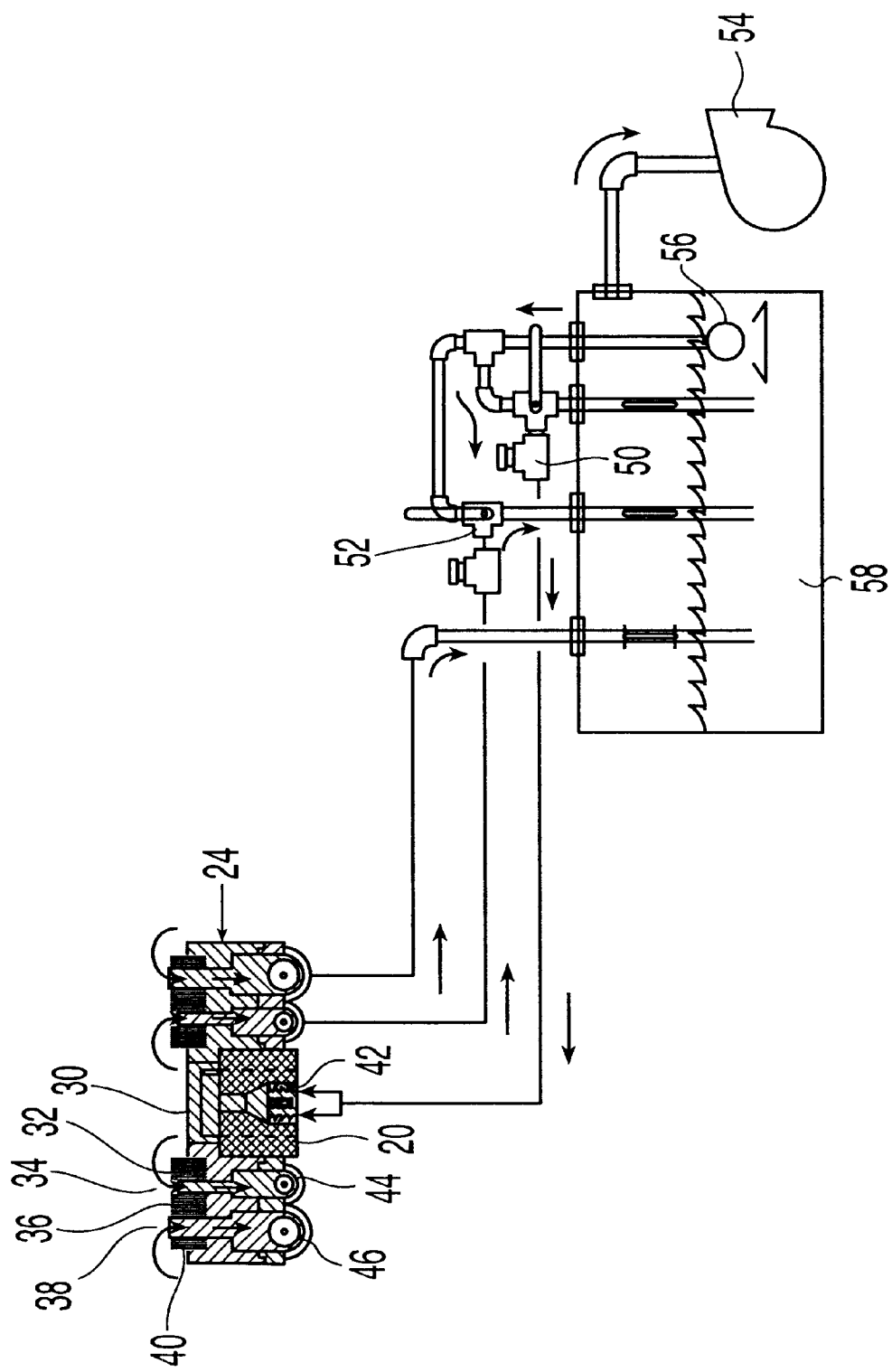
FIG. 9 is a cross-sectional side view of the couplant/vacuum head, flow paths, valves, couplant source, and vacuum, according to the present invention, configured for lower surface scanning.

FIG. 9 shows a cross-sectional side view of the couplant/vacuum head 24, similar to FIG. 5, with additional flow paths, valves, couplant source, and a vacuum. Valve 50 is positioned so that water flows to port 42 at the bottom of the transducer holding block 20. Valve 52 is moved so that a vacuum created by the vacuum 54 is connected to the intermediate region 34. No valve is connected to the outermost recovery region 38, since this region always is subjected to the vacuum from the blower 54. The couplant is drawn through a pump 56 and is supplied from the couplant supply source 58 to the port 42 at the bottom of the transducer holder block 20. Any couplant that flows outwards over the elongated annular inner brush seal 32 into the intermediate region 34 is drawn back through tubes 44 and valve 54 into the couplant supply source 58.

Any couplant that flows over the intermediate brush seal 36, enters the outermost recovery region 38 formed by the outer brush seal 40 spaced outwardly from the intermediate brush seal 36. The vacuum created by the blower 54 draws the couplant back through the tubes 46 to the couplant supply source 58 from the outermost recovery region 38. As a result of the foregoing configuration, any couplant that overflows the elongated annular inner brush seal 32 or the intermediate brush seal 36 due to surface irregularities or raised fastener heads is recovered in both the intermediate and outermost recovery regions 34 and 38 that are both connected to a vacuum 54.

Figure 10:
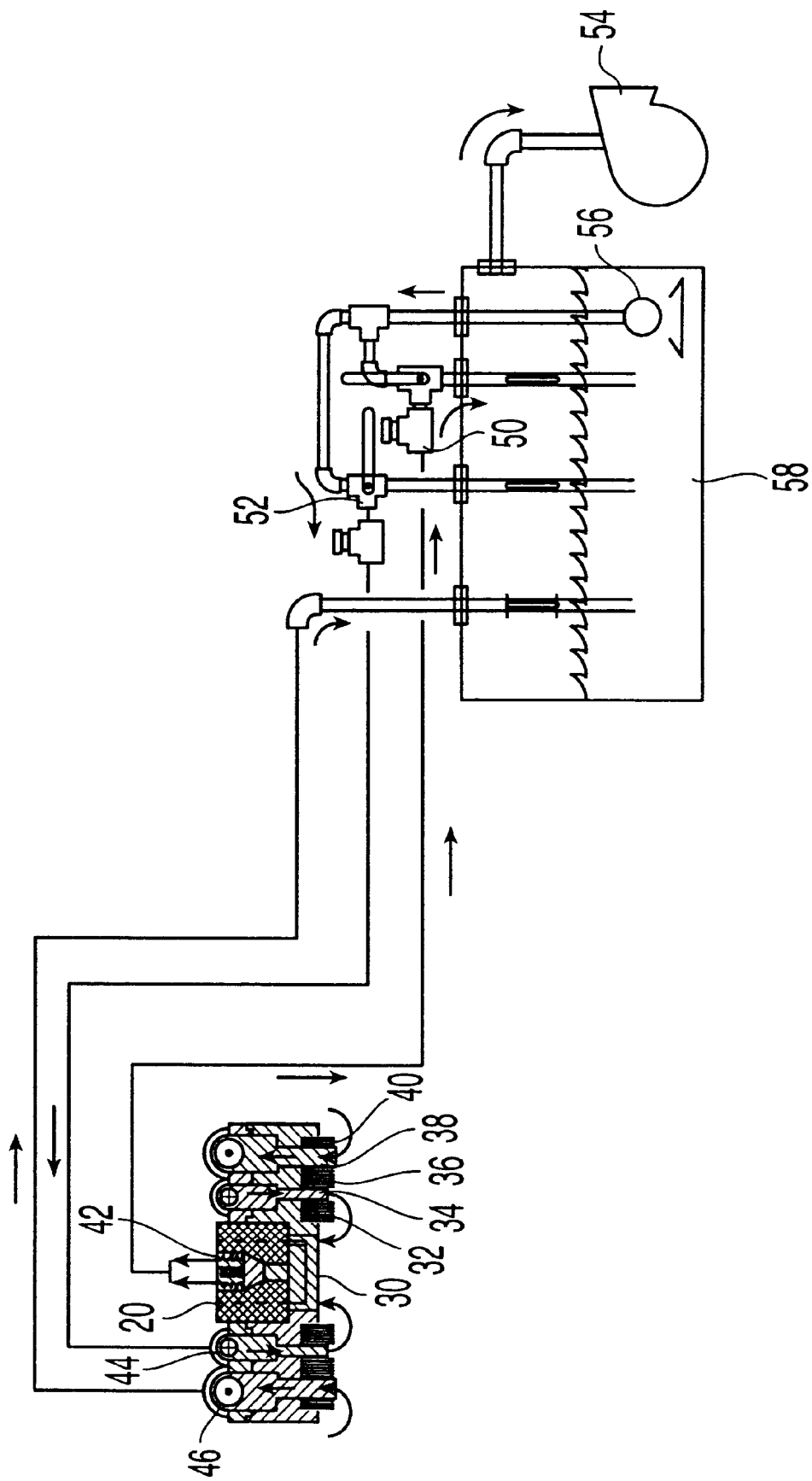
FIG. 10 is a cross-sectional side view of the couplant/vacuum head, flow paths, valves, couplant source, and vacuum, according to the present invention, configured for upper surface scanning.

Referring to FIG. 10, a cross-sectional side view of the couplant/vacuum head 24, similar to FIG. 7, with additional flow paths, valves, couplant source, and a vacuum is shown configured for upper surface inspection. The couplant is supplied from the couplant supply source 58 through valve 52 and tubes 44 to the intermediate region 34. The innermost transducer region 30 and the outermost recovery region 38 are connected to blower 54 and to the vacuum created thereby. Excess couplant flowing into the outermost recovery region 38 is drawn back to the couplant supply source 58 by the high airflow created by the blower 54. Similarly, couplant that flows inwards under the inner brush seal 32 is drawn through the port 42 in the transducer holding block 20 through the valve 50 by the vacuum 54.

The various components of the ultrasonic inspection apparatus 100 are illustrated in the block diagram shown in FIG. 11. The cart 60 contains a data acquisition/computer system, motion control system, and an emergency stop. The automatic scanner assembly 62 supports the couplant/vacuum head 24, and is connected to the cart 60. The cart 60 sends signals to the scanner assembly 62 to control the position of the couplant couplant/vacuum head 24. These signals include a two dimensional position control signals including an x-axis and a y-axis position control signals. The couplant/vacuum head 24 also receives a vacuum control signal and extend and retract signals from the cart 60.

A vacuum source 54 is provided and is connected to the couplant supply source 58, shown in greater detail in FIGS. 9 and 11. The vacuum source 54 is also connected to the cart 60 to enable the control of the scanner assembly 62. Three flow paths to the couplant delivery/recovery head are provided, one each for the recovery region 38, the intermediate region 34, and the innermost transducer region 30. Two channels connect the two transducers 22 in the transducer holder block 20 of the couplant/vacuum head 24 to the cart 60.

Figure 12:
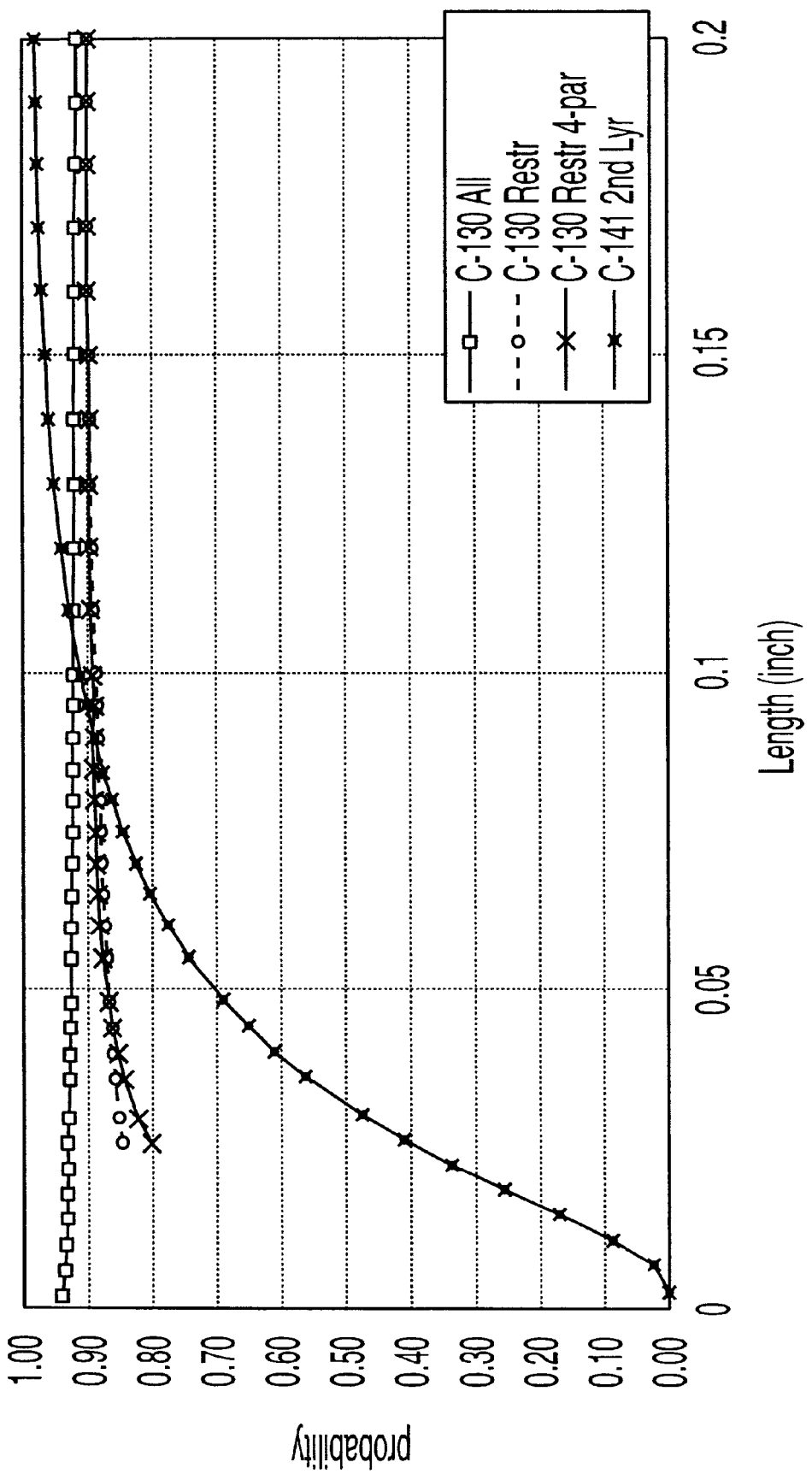
FIG. 12 is a graph of the probability of detecting a flaw according to the present invention.

Testing of the ultrasonic inspection apparatus 100 can be used to produce a graph, as shown in FIG. 12, of a probability of detecting a flaw. The plotted probability of detection is a function of the size of the flaw. The probability of detecting flaws increases, as the flaws get larger. The probability of detection graph can be used to provide a level of confidence that a certain defect or flaw size can be detected.

Aircraft are commonly assembled using thousands of fasteners. For example, approximately 8,800 fasteners are used in the construction of an upper wing surface, and over 10,000 fasteners are used in the construction of a lower wing surface of a C-130 airplane. Over the life of the aircraft these fasteners must be regularly inspected to evaluate the integrity and air-worthiness of the aircraft. The ultrasonic inspection apparatus 100 can be used to perform non-invasive flaw and corrosion inspection of many portions of an airplane, such as the first and second layers of wing splice joints, center wing stringers, rainbow fitting attach areas, and thin and thick multi-layer structures.

Figure 13:
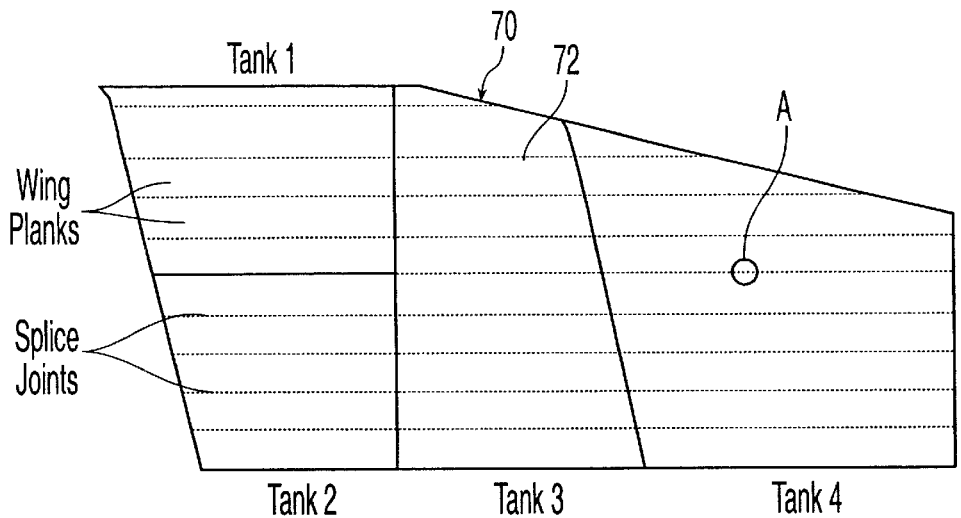
FIG. 13 is an upper view of a portion of a wing having splice joints shown in phantom.
Figure 14:
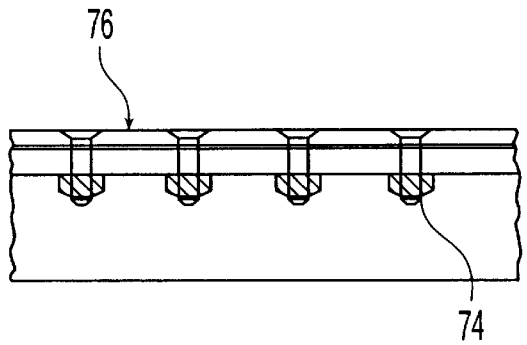
FIG. 14 is a partial side view of a splice joint shown in FIG. 13.
Figure 15:
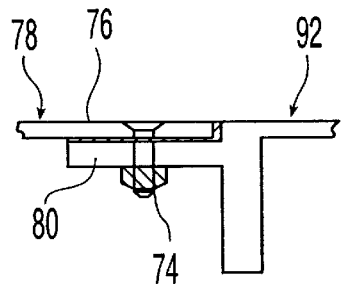
FIG. 15 is a partial cross-sectional view of the splice joint shown in FIGS. 13 and 14.

The operation of the ultrasonic inspection apparatus 100 will now be described with regard to wing Spanish splice joints for a C-141 airplane. Cracks in the second layer 80 of the spanwise splice joint are considered a life-limiting feature, i.e. in-flight failure of the splice joint could be catastrophic. FIG. 13 shows an upper view of a portion of the C-141 wing 70 with splice joints 72 shown in phantom. FIGS. 14 and 15 are a side and cross-sectional view of the splice joint 72, respectively. The fasteners 74 extend through the first layer 76 of one wing plank 78 and a second layer 80 of an adjacent wing plank 82.

For lower surface inspection, the ultrasonic inspection apparatus is configured so that couplant flows into the port 42 at the bottom of the transducer holder block 20, from a pump 56, as shown in FIG. 9. The couplant rises filling the cavity of the innermost transducer region 30 and then flows outwards over the elongated annular inner brush seal 32 into the intermediate region 34. The vacuum 54 draws the overflowing couplant from the innermost transducer region 30 is drawn from the surface being inspected and returns it to the couplant supply source 58 through the tubes 44.

Couplant flowing over the intermediate brush seal 36 enters the outermost recovery region 38, as shown in FIG. 9. The vacuum 54 draws the couplant flowing into the outermost recovery region back to the couplant supply source 58 through tubes 46. The tubes 46 leading from the outermost recovery region 38 have a larger diameter than the diameter of the tubes 44 leading form the intermediate region 34. The high airflow through the tubes 46 also helps dry the surface being inspected.

For upper surface inspection, couplant is supplied through the tubes 44 to the intermediate region 34. The vacuum 54 is connected to both the innermost transducer region 30 and the outermost recovery region 38. Excess couplant flowing into the outermost recovery region 38 is drawn back through the tubes 46 to the couplant supply source 58 by the high airflow created by the vacuum 54. Similarly, couplant flowing inwards under the inner brush seal 32 is drawn through the port 42 in the transducer holding block 20 by the vacuum 54.

Figure 16:
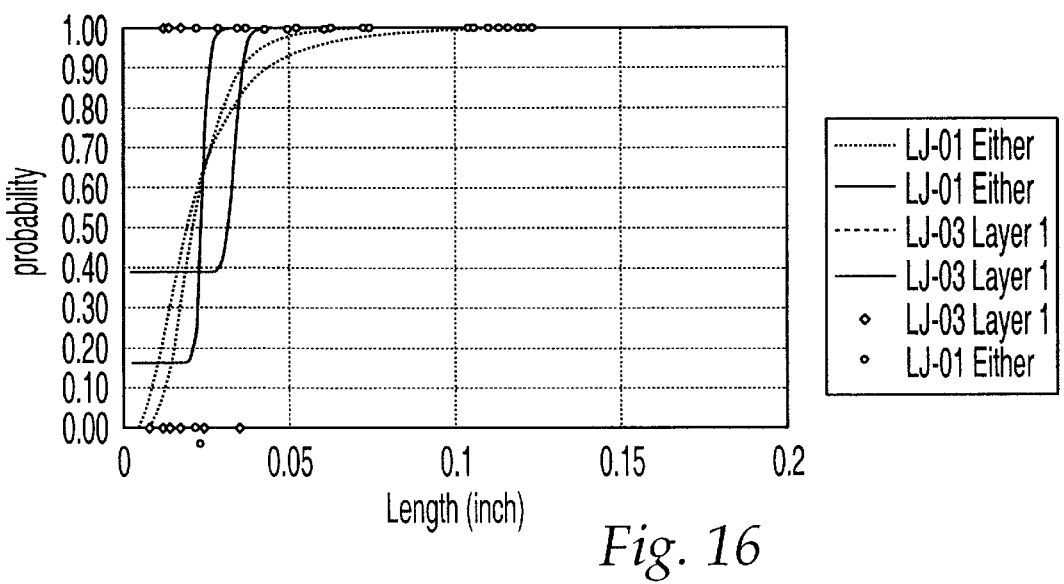
FIG. 16 is a graph of the probability of detecting a flaw in a splice joint of a wing of aC-141 airplane, produced using the present invention.

In use the ultrasonic inspection apparatus 100 is attached to the wing of the C-141 so that it travels along the juncture of two adjacent wing planks 78 and 82. Referring to the probability of detection graph shown in FIG. 16, the ultrasonic inspection apparatus 100 of the present invention has a 90% probability of detecting flaws in the second layer 80 of 0.073 inches or greater, and a 90% probability of detecting flaws in the first layer 76 of 0.040 inches or greater. Furthermore, the ultrasonic inspection apparatus 100 falsely detected a flaw less than 1% of the time. As a result the time interval between inspections can be increased, thereby producing significant cost savings for both the inspection and maintenance and the downtime of the airplane.

The operation of the ultrasonic inspection apparatus 100 can be tailored to the part being inspected. This is accomplished by adjusting a number of variables, including the gain of the transducers, the time and gate delays for the transducers, the head pressure for the couplant supply 58, and the surface being inspected. The gain, time delay and gate delay appear to be the most important for achieving good inspection in both layers of a wingspan splice joint. In order to assure a good inspection, the gain should be maintained at a nominal or higher level, and the time delay and gate delay values should not deviate from the nominal level in the same direction, i.e., both high or both low.

As an example, to assure good inspection results, allowable deviations from the nominal procedure levels (denoted as 0) are for the Gain to be in the interval [0, +6 dB] combined with one of two conditions for the Time Delay and the Gate Delay. The first condition is that the Time Delay be in the interval [−0.06 inch, 0] and the Gate Delay be in the interval [0,+0.09 inch]. Condition 2 is that Time Base Delay be in the interval [0, 0.06 inch] and Gate Delay be in the interval [−0.09 inch, 0]. These results are made with regard to the C-141 second layer inspections on the wing spanwise splices. The dimensions and materials of other inspection sites may yield different desired values for the foregoing variables.

The length and width of the brush seals, as well as what they are made of, significantly affects the size of the fasteners and the surface irregularities that the ultrasonic inspection system can be used on and still provide satisfactory couplant removal.

Having described several embodiments of the method and apparatus for non-destructive ultrasonic inspection in accordance with the present invention, it is believed that other modifications, variations and changes will be suggested to those skilled in the art in view of the description set forth above. For example, the couplant need not be water, but could be another fluid. It is therefore to be understood that all such variations, modifications and changes are believed to fall within the scope of the invention as defined in the appended claims.

What is claimed is:

1. An acoustic inspection apparatus for detecting flaws in an upper surface of a workpiece, comprising:

a transducer that emits sound waves and receives reflected waves from said workpiece, a first annular brush seal disposed around a head of said transducer and forming an inner transducer region;

a second annular intermediate brush seal disposed around said first annular brush seal and forming an intermediate region between said first and second annular brush seals;

a third annular outermost brush seal disposed around said second annular brush seal and forming an outermost recovery region between said second and third annular brush seals; said first, second and third brush seals being co-planar, a couplant supply source providing fluid couplant into said intermediate region; and a vacuum connected to said inner transducer region and said outermost recovery region to draw said couplant away from said workpiece and return said couplant to said couplant supply source.

2. An acoustic inspection apparatus for detecting flaws in an upper surface of a workpiece, as recited in claim 1, wherein said transducer is mounted in a transducer head block.

3. An acoustic inspection apparatus for detecting flaws in an upper surface of a workpiece, as recited in claim 1, wherein said first annular brush seal, said second annular intermediate brush seal, and said third annular outermost brush seal are mounted on a brush subassembly.

4. An acoustic inspection apparatus for detecting flaws in an upper surface of a workpiece, as recited in claim 3, wherein said transducer is mounted in a transducer head block, said transducer block fitting into said brush subassembly.

5. An acoustic inspection apparatus for detecting flaws in an upper surface of a workpiece, as recited in claim 1, wherein said couplant is supplied to said intermediate region through tubes having a first diameter, and said vacuum is connected to said outermost recovery region through tubes having a second diameter larger than said first diameter.

6. An acoustic inspection apparatus for detecting flaws in an upper surface of a workpiece, as recited in claim 4, wherein said transducer, said transducer head block and said brush subassembly form a couplant/vacuum head assembly.

7. An acoustic inspection apparatus for detecting flaws in an upper surface of a workpiece, as recited in claim 6, wherein said couplant/vacuum head assembly is mounted on an automatic scanning apparatus so that said couplant/vacuum assembly moves across a surface of the workpiece.

8. An acoustic inspection apparatus for detecting flaws in an upper surface of a workpiece, as recited in claim 4, wherein said transducer head block supports two transducers.

9. An acoustic inspection apparatus for detecting flaws in an upper surface of a workpiece, as recited in claim 8, wherein said two transducers are mounted at opposing 20 degree angles.

10. An acoustic inspection apparatus for detecting flaws in an upper surface of a workpiece, as recited in claim 8, wherein said two transducers are mounted perpendicular to the surface of the workpiece.

11. An acoustic inspection apparatus for detecting flaws in an upper surface of a workpiece, as recited in claim 1, wherein a gain of said transducer is maintained at at least a nominal level, a time delay and gate delay for said the transducer do not deviate from said nominal level in the same direction.

12. An acoustic inspection apparatus for detecting flaws in an upper surface of a workpiece, as recited in claim 11, wherein said workpiece has spanwise splices, and said gain is between 0 dB and +6 dB, said time delay is between –0.06 inch and 0 inch, and said gate delay is between 0 inch and +0.09 inch.

13. An acoustic inspection apparatus for detecting flaws in an upper surface of a workpiece, as recited in claim 11, wherein said workpiece has spanwise splices, and said gain is between 0 dB and +6 dB, said time delay is between 0 inch and 0.06 inch, and said gate delay is between –0.09 inch and 0 inch.

14. An acoustic inspection apparatus for detecting flaws in a lower surface of a workpiece, comprising:
    a transducer that emits sound waves and receives reflected waves from said workpiece, a first annular brush seal disposed around a head of said transducer and forming an inner transducer region;
    a second annular intermediate brush seal disposed around said first annular brush seal and forming an intermediate region between said first and second annular brush seals;
    a third annular outermost brush seal disposed around said second annular brush seal and forming an outermost recovery region between said second and third annular brush seals; said first, second and third brush seals being co-planar,
    a couplant supply source providing fluid couplant into said inner transducer region; and
    a vacuum connected to said intermediate region and said outermost recovery region to draw said couplant away from said workpiece and return said couplant to said couplant supply source.

15. An acoustic inspection apparatus for detecting flaws in a lower surface of a workpiece, as recited in claim 14, wherein said transducer is mounted in a transducer head block.

16. An acoustic inspection apparatus for detecting flaws in a lower surface of a workpiece, as recited in claim 14, wherein said first annular brush seal, said second annular intermediate brush seal, and said third annular outermost brush seal are mounted on a brush subassembly.

17. An acoustic inspection apparatus for detecting flaws in a lower surface of a workpiece, as recited in claim 16, wherein said transducer is mounted in a transducer head block, said transducer block fitting into said brush subassembly.

18. An acoustic inspection apparatus for detecting flaws in a lower surface of a workpiece, as recited in claim 14, wherein said vacuum is connected to said intermediate region through tubes having a first diameter, and to said outermost recovery region through tubes having a second diameter larger than said first diameter.

19. An acoustic inspection apparatus for detecting flaws in a lower surface of a workpiece, as recited in claim 17, wherein said transducer, said transducer head block and said brush subassembly form a couplant/vacuum head assembly.

20. An acoustic inspection apparatus for detecting flaws in a lower surface of a workpiece, as recited in claim 19, wherein said couplant/vacuum head assembly is mounted on an automatic scanning apparatus so that said couplant/vacuum assembly moves across a surface of the workpiece.

21. An acoustic inspection apparatus for detecting flaws in a lower surface of a workpiece, as recited in claim 17, wherein said transducer head block supports two transducers.

22. An acoustic inspection apparatus for detecting flaws in a lower surface of a workpiece, as recited in claim 21, wherein said two transducers are mounted at opposing 20 degree angles.

23. An acoustic inspection apparatus for detecting flaws in a workpiece, as recited in claim 21, wherein said two transducers are mounted perpendicular to the surface of the workpiece.

24. An acoustic inspection apparatus for detecting flaws in a lower surface of a workpiece, as recited in claim 14, wherein a gain of said transducer is maintained at at least a nominal level, a time delay and gate delay for said the transducer do not deviate from said nominal level in the same direction.

25. An acoustic inspection apparatus for detecting flaws in a lower surface of a workpiece, as recited in claim 24, wherein said workpiece has spanwise splices, and said gain is between 0 dB and +6 dB, said time delay is between –0.06 inch and 0 inch , and said gate delay is between 0 inch and +0.09 inch.

26. An acoustic inspection apparatus for detecting flaws in a lower surface of a workpiece, as recited in claim 24, wherein said workpiece has spanwise splices, and said gain is between 0 dB and +6 dB, said time delay is between 0 inch and 0.06 inch, and said gate delay is between –0.09 inch and 0 inch.

27. An acoustic inspection apparatus for detecting flaws in a lower surface of a workpiece, as recited in claim 14, wherein said transducer is an ultrasonic transducer.

28. An acoustic inspection apparatus for detecting flaws in an upper surface of a workpiece, as recited in claim 1, wherein said transducer is an ultrasonic transducer.

29. A method of acoustically inspecting an upper surface, comprising the steps of:
    emitting sound waves from a transducer and receiving reflected waves from a workpiece;
    providing a vacuum to an inner transducer region formed by a first annular brush seal disposed around a head of said transducer;
    providing fluid couplant to an intermediate region formed by a second annular intermediate brush seal disposed around said first annular brush seal; and
    providing a vacuum to an outermost recovery region formed between said second and third annular brush seals, said first, second and third brush seals being co-planar,
    said vacuum connected to said inner transducer region and said outermost recovery region drawing said couplant away from said workpiece and returning said couplant to said couplant supply source.

30. A method of acoustically inspecting an upper surface, as recited in claim 29, comprising the further step of mounting said transducer in a transducer head block.

31. A method of acoustically inspecting an upper surface, as recited in claim 29, comprising the further step of mounting said first annular brush seal, said second annular intermediate brush seal, and said third annular outermost brush seal on a brush subassembly.

32. A method of acoustically inspecting an upper surface, as recited in claim 31, comprising the further step of mounting said transducer in a transducer head block, and fitting said transducer block into said brush subassembly.

33. A method of acoustically inspecting an upper surface, as recited in claim 29, wherein said step of supplying couplant to said intermediate region is performed by transferring said couplant through tubes having a first diameter, and said step of providing a vacuum to said outermost recovery region is performed through tubes having a second diameter larger than said first diameter.

34. A method of acoustically inspecting an upper surface, as recited in claim 32, wherein said transducer, said transducer head block and said brush subassembly form a couplant/vacuum head assembly.

35. A method of acoustically inspecting an upper surface, as recited in claim 34, further comprising the steps of mounting said couplant/vacuum head assembly on an automatic scanning apparatus, and moving said couplant/vacuum assembly across a surface of the workpiece.

36. A method of acoustically inspecting an upper surface, as recited in claim 32, wherein said transducer head block supports two transducers.

37. A method of acoustically inspecting an upper surface, as recited in claim 36, wherein said two transducers are mounted at opposing 20 degree angles.

38. A method of acoustically inspecting an upper surface, as recited in claim 36, wherein said two transducers are mounted perpendicular to the surface of the workpiece.

39. A method of acoustically inspecting an upper surface, as recited in claim 29, further comprising the steps of maintaining a gain of said transducer at at least a nominal level, maintaining a time delay and gate delay for said transducer so as not to deviate from said nominal level in a same direction.

40. A method of acoustically inspecting an upper surface, as recited in claim 39, wherein said workpiece has spanwise splices, and said gain is between 0 dB and +6 dB, said time delay is between −0.06 inch and 0 inch, and said gate delay is between 0 inch and +0.09 inch.

41. A method of acoustically inspecting an upper surface, as recited in claim 39, wherein said workpiece has spanwise splices, and said gain is between 0 dB and +6 dB, said time delay is between 0 inch and 0.06 inch, and said gate delay is between −0.09 inch and 0 inch.

42. A method of acoustically inspecting a lower surface, comprising the steps of:

emitting sound waves from a transducer and receiving reflected waves from a workpiece;

providing fluid couplant to an inner transducer region formed by a first annular brush seal disposed bound a head of said transducer; and providing a vacuum to an intermediate region formed by a second annular intermediate brush seal disposed around said first annular brush seal, and an outermost recovery region formed between said second and third annular brush seals, said first, second and third brush seals being co-planar, and said vacuum connected to said intermediate region and said outermost recovery region drawing said couplant away from said workpiece and returning said couplant to said couplant supply source.

43. A method of acoustically inspecting a lower surface, as recited in claim 42, comprising the further step of mounting said transducer in a transducer head block.

44. A method of acoustically inspecting a lower surface, as recited in claim 42, comprising the further step of mounting said first annular brush seal, said second annular intermediate brush seal, and said third annular outermost brush seal on a brush subassembly.

45. A method of acoustically inspecting a lower surface, as recited in claim 44, comprising the further step of mounting said transducer in a transducer head block, and fitting said transducer block into said brush subassembly.

46. A method of acoustically inspecting a lower surface, as recited in claim 42, wherein said step providing a vacuum to said intermediate is performed through tubes having a first diameter, and said step of providing a vacuum to said outermost recovery region is performed through tubes having a second diameter larger than said first diameter.

47. A method of acoustically inspecting a lower surface, as recited in claim 45, wherein said transducer, said transducer head block and said brush subassembly form a couplant/vacuum head assembly.

48. A method of acoustically inspecting a lower surface, as recited in claim 47, further comprising the steps of mounting said couplant/vacuum head assembly on an automatic scanning apparatus, and moving said couplant/vacuum assembly across a surface of the workpiece.

49. A method of acoustically inspecting a lower surface, as recited in claim 45, wherein said transducer head block supports two transducers.

50. A method of acoustically inspecting a lower surface, as recited in claim 49, wherein said two transducers are mounted at opposing 20 degree angles.

51. A method of acoustically inspecting a lower surface, as recited in claim 49, wherein said two transducers are mounted perpendicular to the surface of the workpiece.

52. A method of acoustically inspecting a lower surface, as recited in claim 42, further comprising the steps of maintaining a gain of said transducer at at least a nominal level, maintaining a time delay and gate delay for said transducer so as not to deviate from said nominal level in a same direction.

53. A method of acoustically inspecting a lower surface, as recited in claim 52, wherein said workpiece has spanwise splices, and said gain is between 0 dB and +6 dB, said time delay is between −0.06 inch and 0 inch, and said gate delay is between 0 inch and +0.09 inch.

54. A method of acoustically inspecting a lower surface, as recited in claim 52, wherein said workpiece has spanwise splices, and said gain is between 0 dB and +6 dB, said time delay is between 0 inch and 0.06 inch, and said gate delay is between −0.09 inch and 0 inch.

* * * * *